United States Patent [19]

Ohsaka et al.

[11] 4,296,265

[45] Oct. 20, 1981

[54] PROCESS FOR PREPARING HEXAFLUOROPROPENE OLIGOMERS

[75] Inventors: Yohnosuke Ohsaka, Takatsuki; Takashi Tohzuka, Settsu, both of Japan

[73] Assignee: Daikin Kogyo Co., Ltd., Osaka, Japan

[21] Appl. No.: 170,151

[22] Filed: Jul. 18, 1980

[30] Foreign Application Priority Data

Jul. 19, 1979 [JP] Japan .................................. 54-91849
Aug. 15, 1979 [JP] Japan ................................ 54-103713

[51] Int. Cl.³ ............................................ C07C 17/26
[52] U.S. Cl. ..................................... 570/138; 570/139
[58] Field of Search ................................ 570/138, 139

[56] References Cited

U.S. PATENT DOCUMENTS

4,042,638  8/1977  Ozawa et al. ........................ 570/138

FOREIGN PATENT DOCUMENTS

50-117705  9/1975  Japan .................................. 570/138

*Primary Examiner*—Delbert E. Gantz
*Assistant Examiner*—Joseph A. Boska
*Attorney, Agent, or Firm*—Birch, Stewart, Kolasch and Birch

[57] ABSTRACT

Hexafluoropropene oligomers are prepared from hexafluoropropene in a high conversion by contacting gaseous hexafluoropropene with a catalyst comprising an alkali metal fluoride supported on activated charcoal or nickel oxide.

5 Claims, No Drawings

PROCESS FOR PREPARING HEXAFLUOROPROPENE OLIGOMERS

This invention relates to a process for preparing hexafluoropropene oligomers.

Hexafluoropropene oligomers, i.e. the dimer and trimer of hexafluoropropene, are useful as solvents or intermediates in the synthesis of surfactants.

It is known that hexafluoropropene oligomers can be prepared by oligomerizing hexafluoropropene in an aprotic solvent in the presence of a base or a fluoride ion. In this reaction, however, the solvent is required to be nonaqueous and must be dehydrated or dried prior to the use. The oligomers are insoluble in the solvent and form one phase at the bottom of the reactor so that it seems easy to separate the oligomers from the solvent by discharging the oligomers from the bottom of the reactor. But, the oligomers are in fact contaminated with the solvent so that washing or distillation is needed for elimination of the contaminant. In addition, the alkali metal fluoride must be separated and recovered from the oligomers for re-utilization. These operations are quite troublesome.

It is also known that oligomerization of hexafluoropropene in the absense of any solvent can be effected in an autoclave at about 200° C. This process does not reqire said troublesome operations. However, in this process, the reaction pressure inevitably becomes high, and the reaction time becomes long.

On the other hand, hexafluoropropene oligomers can hardly be obtained in a gaseous phase reaction. For example, when hexafluoropropene is passed through a layer of powdery cesium fluoride at 350° C. with a contact time of 2 minutes, the conversion of hexafluoropropene is as low as 3.5%, or in order to attain the 70% conversion of hexafluoropropene in an autoclave containing cesium fluoride, it takes as long as 87 hours at a temperature of 215° C. under a pressure of 14 atm. [J. Org. Chem., 30,3524(1965)].

It has now been found that the oligomerization of hexafluoropropene in a gaseous phase proceeds with a conversion of several tens % even in a very short contact time when an alkali metal fluoride supported on activated charcoal or nickel oxide is used as the catalyst. This finding is of unexpected nature, because the alkali metal fluoride itself achieves the oligomerization with only a very low conversion or in a very long contact time as stated above.

According to this invention, there is provided a process for preparing hexafluoropropene oligomers with a high conversion in a short contact time which comprises contacting gaseous hexafluoropropene with an alkali metal fluoride supported on activated charcoal or nickel oxide as a catalyst. By such process, hexafluoropropene oligomers can be prepared in a conversion of several tens % at a temperature of about 200° C. in a contact time of about 2 minutes. Since no solvent is used in the process, neither the drying of a solvent nor the separation of a solvent from the reaction mixture is needed. Further, the reaction is a gas phase one, and therefore the catalyst can be separated from the reaction mixture with ease. Furthermore, the catalyst can be prepared by a simple operation.

The catalyst to be used in the process of the present invention may be prepared, for instance, by immersing activated charcoal or nickel oxide in an aqueous solution of an alkali metal fluoride and collecting the carrier from the solution, followed by drying and heating in an inert gas such as nitrogen at a temperature of from the reaction temperature for oligomerization of hexafluoropropene to about 300° C. higher than the oligomerization reaction temperature. Examples of the alkali metal fluoride are cesium fluoride, potassium fluoride, etc.

The content of the alkali metal fluoride in the catalyst may be from about 5 to 100% by weight on the basis of the weight of the carrier. When the carrier is activated charcoal, the alkali metal fluoride content is preferred from about 10 to 100% by weight. When the carrier is nickel oxide, it is favorably from about 5 to 30% by weight.

The reaction temperature is usually from the boiling point of the trimer of hexafluoropropene to be prepared (106° C./1 atm.) to 300° C., preferably from about 150 to 250° C. The reaction pressure may be a reduced, atmospheric or elevated one but not higher than the one under which the trimer is maintained in a gaseous state. The contact time depends on the content of the alkali metal fluoride in the catalyst, the kind of the alkali metal fluoride, the reaction temperature, the reaction pressure, the desired conversion, etc. and is usually from about 30 seconds to 10 minutes. Hexafluoropropene may be introduced into the reactor as such or in a diluted form with an inert gas such as nitrogen, helium or argon.

The present invention will be hereinafter explained in detail by the following Examples wherein % is by weight, unless otherwise indicated.

EXAMPLE 1

Activated charcoal ("Shirasagi CX" manufactured by Takeda Chemical Industries, Ltd.) (30 g) was immersed in a 30% aqueous solution of potassium fluoride. The charcoal was collected by filtration, dried at 100° C. for 20 hours and heated in a nitrogen stream at 350° C. for 5 hours to give a catalyst (43.4 g) comprising potassium fluoride as the active component and activated charcoal as the carrier. The potassium fluoride content was 44.7% on the basis of the weight of the charcoal.

The catalyst (35 g) was charged into a Hastelloy C made reactor of ¾ inch in diameter and 1 m in length and heated in a nitrogen stream at 400° C. Then, hexafluoropropene was passed through the reactor at 200° C. under the atmospheric pressure at a flow rate of 20 ml/min. The discharged gas was collected in a trap cooled with dry ice and subjected to analysis by gas chromatography, mass spectrometry and NMR. The results were as follows:

Conversion of hexafluoropropene: 81% by mole
Composition of the reaction mixture:
  Dimer: 33.8% by mole
  $C_9F_{16}$: 10.0% by mole
  Trimer: 56.2% by mole The trimer comprises a compound of the formula:

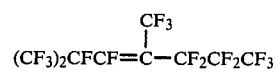

(a mixture of cis- and trans-isomers) in a content of 90.5% by mole. The dimer comprises a compound of the formula: $(CF_3)_2C=CFCF_2CF_3$ and a compound of the formula: $(CF_3)_2CFCF(CF_3)_2$ in contents of 87% by mole and 13% by mole, respectively.

EXAMPLE 2

Activated charcoal in a granular form (30 g) was immersed in a 20% aqueous solution of potassium fluoride. The charcoal was collected by filtration, dried and heated in the same manner as in Example 1 to give a catalyst (36.5 g) comprising potassium fluoride as the active component and activated charcoal as the carrier. The potassium fluoride content was 21% on the basis of the weight of the charcoal.

In the same manner as in Example 1 but using the catalyst as obtained above, the oligomerization of hexafluoropropene was carried out. The results were as follows:

Conversion of hexafluoropropene: 76% by mole
Composition of the reaction mixture:
  Dimer: 32.0% by mole
  $C_9F_{16}$: 8.3% by mole
  Trimer: 59.7% by mole Trimer comprises a compound of the formula:

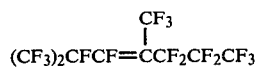

$$(CF_3)_2CFCF=CCF_2CF_2CF_3$$

(a mixture of cis- and trans-isomers) in a content of 88% by mole. The dimer comprises a compound of the formula: $(CF_3)_2C=CFCF_2CF_3$ and a compound of the formula: $(CF_3)_2CFCF(CF_3)_2$ in contents of 87% by mole and 13% by mole, respectively.

EXAMPLE 3

Activated charcoal ("Shirasagi CX" manufactured by Takeda Chemical Industries, Ltd.) (30 g) was immersed in a 13% aqueous solution of cesium fluoride. The charcoal was collected by filtration, dried and heated in the same manner as in Example 1 to give a catalyst (32.8 g) comprising cesium fluoride as the catalyst and activated charcoal as the carrier. The cesium fluoride content was 9.3% on the basis of the weight of the charcoal.

Into a "Pyrex" glass made reactor of 1 inch in diameter and 1 m in length, the catalyst (32.8 g) was charged and heated in a nitrogen stream at 400° C. for 5 hours. Hexafluoropropene was passed through the reactor at 200° C. for 5 hours under atmospheric pressure at a flow rate of 30 ml/min. The discharged gas (60 g) was collected in a trap cooled with dry ice. Thereafter, hexafluoropropene was passed though the reactor at 250° C. for 5 hours. The discharged gas was collected in another trap cooled with dry ice. Each collected gas was analyzed. The results were shown in Table 1.

TABLE 1

| Reaction Temperature (°C.) | Conversion (% by mole) | Composition of discharged gas (% by mole) | | |
|---|---|---|---|---|
| | | Dimer | $C_9F_{16}$ | Trimer |
| 200 | 35 | 60.5 | 8.3 | 31.2 |
| 250 | 63 | 57.8 | 5.3 | 36.9 |

EXAMPLE 4

To a mixture of commercially available nickel oxide (100 g) and cesium fluoride (100 g), deionized water (30 ml) was added, followed by stirring. The mixture was extruded by a sodium press having a nozzle of 5 mm in diameter onto a polytetrafluoroethylene sheet. The extruded mixture was dried in a drying oven at 100° C. for 24 hours and cut into pellets of about 10 mm in length, which were further heated in an electric furnace under a nitrogen atmosphere at 400° C. for 5 hours.

The thus obtained catalyst (85 g) was charged into a "Pyrex" glass made reactor of 1 inch in diameter and 1 m in length and heated in nitrogen stream at 400° C. Hexafluoropropene was passed through the reactor at 200° C. under the atmospheric pressure at a flow rate of 20 ml/min. The discharged gas was collected in a trap cooled with dry ice and subjected to analysis by gas chromatography, mass spectrometry and NMR. The results were as follows:

Conversion of hexafluoropropene: 72% by mole
Composition of the reaction mixture:
  Dimer: 80.5% by mole
  Trimer: 19.5% by mole

EXAMPLE 5

In the same manner as in Example 4 but using potassium fluoride in place of cesium fluoride, the catalyst was prepared, and the reaction was effected at 220° C. under atmospheric pressure at a flow rate of 30 ml/min. The discharged gas was collected and subjected to analysis. The results were as follows:

Conversion of hexafluoropropene: 71% by mole
Composition of the reaction mixture:
Dimer: 83.3% by mole
Trimer: 16.7% by mole

What is claimed is:

1. A process for preparing hexafluoropropene oligomers which comprises contacting gaseous hexafluoropropene with a catalyst comprising an alkali metal fluoride supported on activated charcoal or nickel oxide.

2. The process according to claim 1, wherein the catalyst is an alkali metal fluoride supported on activated charcoal.

3. The process according to claim 1, wherein the catalyst is an alkali metal fluoride supported on nickel oxide.

4. The process according to any one of claims 1 to 3, wherein the alkali metal fluoride is potassium fluoride or cesium fluoride.

5. The process according to claim 1, wherein the reaction temperature is from the boiling point of the trimer of hexafluoropropene to 300° C.

* * * * *